(12) United States Patent  
Greener et al.

(10) Patent No.: US 7,982,087 B2
(45) Date of Patent: Jul. 19, 2011

(54) WOUND DRESSING

(75) Inventors: Bryan Greener, York (GB); Allan Freedline, Miami Beach, FL (US)

(73) Assignee: Smith & Nephew, Inc., Memphis, TN (US)

( * ) Notice: Subject to any disclaimer, the term of this patent is extended or adjusted under 35 U.S.C. 154(b) by 278 days.

(21) Appl. No.: 12/351,541

(22) Filed: Jan. 9, 2009

(65) Prior Publication Data

US 2010/0179463 A1 Jul. 15, 2010

(51) Int. Cl.
*A61F 13/00* (2006.01)
(52) U.S. Cl. ............................................. 602/42; 602/47
(58) Field of Classification Search ............... 602/41–56
See application file for complete search history.

(56) References Cited

U.S. PATENT DOCUMENTS

| | | | |
|---|---|---|---|
| 4,294,240 A | 10/1981 | Thill | |
| 4,418,691 A | 12/1983 | Yannas et al. | |
| 4,664,662 A | 5/1987 | Webster | |
| 4,929,477 A | 5/1990 | Will | |
| 5,267,952 A | 12/1993 | Gardner | |
| 5,489,304 A | 2/1996 | Orgill et al. | |
| 5,716,411 A | 2/1998 | Orgill et al. | |
| 5,720,714 A | 2/1998 | Penrose | |
| 6,333,093 B1 * | 12/2001 | Burrell et al. | 428/194 |
| 6,713,659 B2 | 3/2004 | Bodenschatz et al. | |
| 6,752,794 B2 | 6/2004 | Lockwood et al. | |
| 6,942,628 B1 | 9/2005 | Watson | |
| 7,108,681 B2 | 9/2006 | Gartstein et al. | |
| 7,122,712 B2 * | 10/2006 | Lutri et al. | 602/43 |
| 2001/0034499 A1 | 10/2001 | Sessions et al. | |
| 2003/0050590 A1 | 3/2003 | Kirsch | |
| 2003/0050594 A1 | 3/2003 | Zamierowski | |
| 2003/0108587 A1 | 6/2003 | Orgill et al. | |
| 2004/0073151 A1 | 4/2004 | Weston | |
| 2005/0222544 A1 | 10/2005 | Weston | |
| 2007/0010775 A1 * | 1/2007 | Lutri | 602/43 |
| 2007/0185426 A1 | 8/2007 | Ambrosio et al. | |
| 2007/0185463 A1 | 8/2007 | Mulligan | |
| 2008/0300555 A1 | 12/2008 | Olson et al. | |
| 2009/0105671 A1 | 4/2009 | Daggar et al. | |
| 2010/0010462 A1 * | 1/2010 | Kurata | 604/372 |
| 2010/0249733 A9 * | 9/2010 | Blott et al. | 604/315 |

FOREIGN PATENT DOCUMENTS

| | | |
|---|---|---|
| GB | 821959 A | 10/1959 |
| WO | WO9010424 A1 | 9/1990 |
| WO | WO2008039839 A2 | 4/2008 |

OTHER PUBLICATIONS

J. Wesley et al., 'Clinical Evaluation of Epigard, A New Synthetic Substitute for Homograft and Heterograft Skin,' The Journal of Trauma, vol. 13, No. 4, 1973, pp. 374-383.
Joanne Stewart, PhD., 'Next Generation Products for Wound Management,' World Wide Wounds, Nov. 2002, 13 pages.

* cited by examiner

*Primary Examiner* — Michael A. Brown
(74) *Attorney, Agent, or Firm* — Fish & Richardson P.C.

(57) ABSTRACT

A wound dressing includes a substantially transparent upper layer, an absorbent layer comprising a plurality of apertures arranged in a lattice pattern, and a low-adherent wound contact layer provided with a plurality of apertures arranged in a lattice pattern such the apertures of this layer are congruent with the apertures of the absorbent layer.

12 Claims, 7 Drawing Sheets

WOUND DRESSING

TECHNICAL FIELD

This invention relates to wound dressings.

BACKGROUND

Health care professionals have previously had the choice of using dressings that allow the wound to be visualized or dressings that can absorb fluid, with some of these dressings also offering a degree of physical/bacterial protection. However, there has not been a dressing available that combines all these features satisfactorily.

Wound dressings have been described in "Films or Fabrics: is it time to re-appraise postoperative dressings?" *British Journal of Nursing*, 2005, Vol 14, No 19, pp S15-S20, as preferably having all of the following characteristics.
 1. Skin-friendly
 2. Biodegradable
 3. Compact
 4. Non-adherent to wound
 5. Augments healing
 6. Maintains wound integrity
 7. 'Attractive'
 8. Provide visibility of: strike-through, peri-wound area and wound area
 9. Cost-effective
 10. Protective against physical damage, dirt and infection
 11. Absorbent
 12. Provide longer than 24 hours wear
 13. Stays in place
 14. 'Waterproof': Showering, Moisture and Incontinence
 15. Easy on—easy off
 16. Range of shapes and sizes

SUMMARY

A wound dressing combines absorbency properties with the ability to monitor the wound's progress, without the need to lift the dressing or disturb the wound.

According to a first aspect, when in situ on a subject the dressing includes a substantially transparent upper layer; an absorbent layer comprising a plurality of apertures arranged in a lattice pattern; and a low-adherent wound contact layer provided with a plurality of apertures arranged in a lattice pattern such the apertures of this layer are congruent with the apertures of the absorbent layer.

The components of the dressing create an optimum environment for healing by controlling moisture balance, absorbing wound discharge and limiting the build-up of fluid under the dressing. This minimizes both the potential for maceration and the number of dressing changes needed. The dressing further provides visibility of the wound in-situ.

The dressing is particularly advantageous for application to, for instance, low to moderate exuding post-operative wounds, lacerations, cuts, abrasion and minor burns.

This transparent upper layer provides the healthcare professional with the ability to carry out regular assessments of the peri-wound area and the wound itself without the need to lift or remove the dressing. This allows them to react early to signs that could potentially delay the healing process. Encouraging healing and reducing the chance of infection can lead to shorter recovery times and lower treatment costs.

The material used to form the transparent top layer is advantageously characterized by a high Moisture Vapor Transmission Rate (MVTR), thereby allowing unwanted moisture to transpire and helps prevent infection and maceration.

The material used to form the transparent top layer is further advantageously characterized by being waterproof, thereby enabling the patient to shower/bathe with the dressing in situ.

The material used to form the transparent upper layer is further advantageously characterized by providing a barrier against bacteria, including methicillin-resistant *staphylococcus aureus* (MRSA). This will reduce the incidences of surgical site infections (SSI) and healthcare associated infections (HAI), reducing possible associated costs to healthcare provider and extended hospital stay for the patient.

The transparent upper layer further advantageously acts as a barrier to water and dirt.

The transparent upper layer can be provided as a film. In embodiments of the invention the layer is a polyurethane film.

The peripheral edges of the transparent upper layer extend beyond the peripheral edges of the absorbent layer. The underside of the transparent upper layer is coated with an adhesive, such as an acrylic adhesive, in order to secure this layer to the absorbent layer and also to the peri-wound area.

The adhesive can be spread in a pattern to increase breathability of the film and improve comfort upon removal.

Advantageously the adhesive used is a low allergy. This type of adhesive reduces the trauma upon removal of the dressings and/or lessens the risk of an allergic reaction.

The dressing is designed to be easy to apply and can be removed in one piece.

The dressing does not require secondary retention.

The highly absorbent layer allows for the lateral spread of wound exudate across the lattice to maximize absorbency without impairing visibility, reducing the risk of skin maceration and minimizing the number of dressing changes for cost effective care.

TABLE 1

Comparative absorbency testing results

| Product | Total Absorption (g/100 cm²) Mean Results |
|---|---|
| OPOV* | 32 |
| OPO** | 21 |
| Tegaderm + Pad | 23 |
| Leukomed T Plus | 22 |
| Mepore | 21 |
| Tegaderm Absorbent Clear | 11 |

*Report Title: Opsite Post-Op Visible. Evaluation or PO samples (DS/07/209/R1) Claims support ref 15
**Report Title: Competitor testing Opsite Post-OP (DS/07/115/R1). Claims support Ref 1

In advantageous embodiments of the invention the absorbent layer comprises a foam, the physical properties of which provides protection and cushioning to the wound site from physical damage, leading to decreased time to healing, and allowing the patient to regain a 'normal' lifestyle as quickly as possible.

The low-adherent wound contact layer is advantageously provided with apertures in a lattice design which substantially mirrors that of the design for the absorbent layer, such that when the wound-contact layer and the absorbent layer are in contact, the apertures are substantially congruent. This facilitates the transfer of the wound exudate into the absorbent layer and ensures visibility through the absorbent layer and the wound contact layer to the wound.

The apertures provided in the absorbent layer and the wound contact layer can be hole-punched. The two layers can be assembled and then hole-punched or alternatively hole-punched prior to assembly, although this makes the assembly more complicated as the apertures need to be lined up correctly in order to ensure optimum absorbency and visibility of the dressing.

The apertures can be provided in various sizes and/or shapes and/or patterns.

The aperture size is selected to be small enough to allow the exudate to easily reach an absorbent strut but large enough to allow reasonable visibility. For example, the absorbent layer has an absorbent area of not more than 50% of the total area covered, preferably not more than 40%, more preferably not more than 30%, with a repeat pattern of no less than 5 mm in x or y direction, preferably no less than 10 mm in x or y direction, and no greater than 30 mm in x or y direction, preferably no greater than 50 mm in x or y direction.

The dressing is advantageously provided in a range of sizes allowing clinicians to apply a suitable size dressing to a variety of wounds shapes and sizes.

The dressing can be supplied individually wrapped and sterile.

According to a second aspect, a method includes manufacturing the dressing by hole punching an absorbent layer and a wound contact layer of a wound dressing such that the absorbent layer defines a plurality of apertures arranged in a lattice pattern and the wound contact layer defines a plurality of apertures arranged in a lattice pattern, and arranging the absorbent layer between a transparent layer and the wound contact layer. The apertures of the wound contact layer are congruent with the apertures of the absorbent layer.

According to a third aspect, there is provided a wound dressing or method of manufacturing thereof as substantially herein described with reference to the accompanying Figures.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
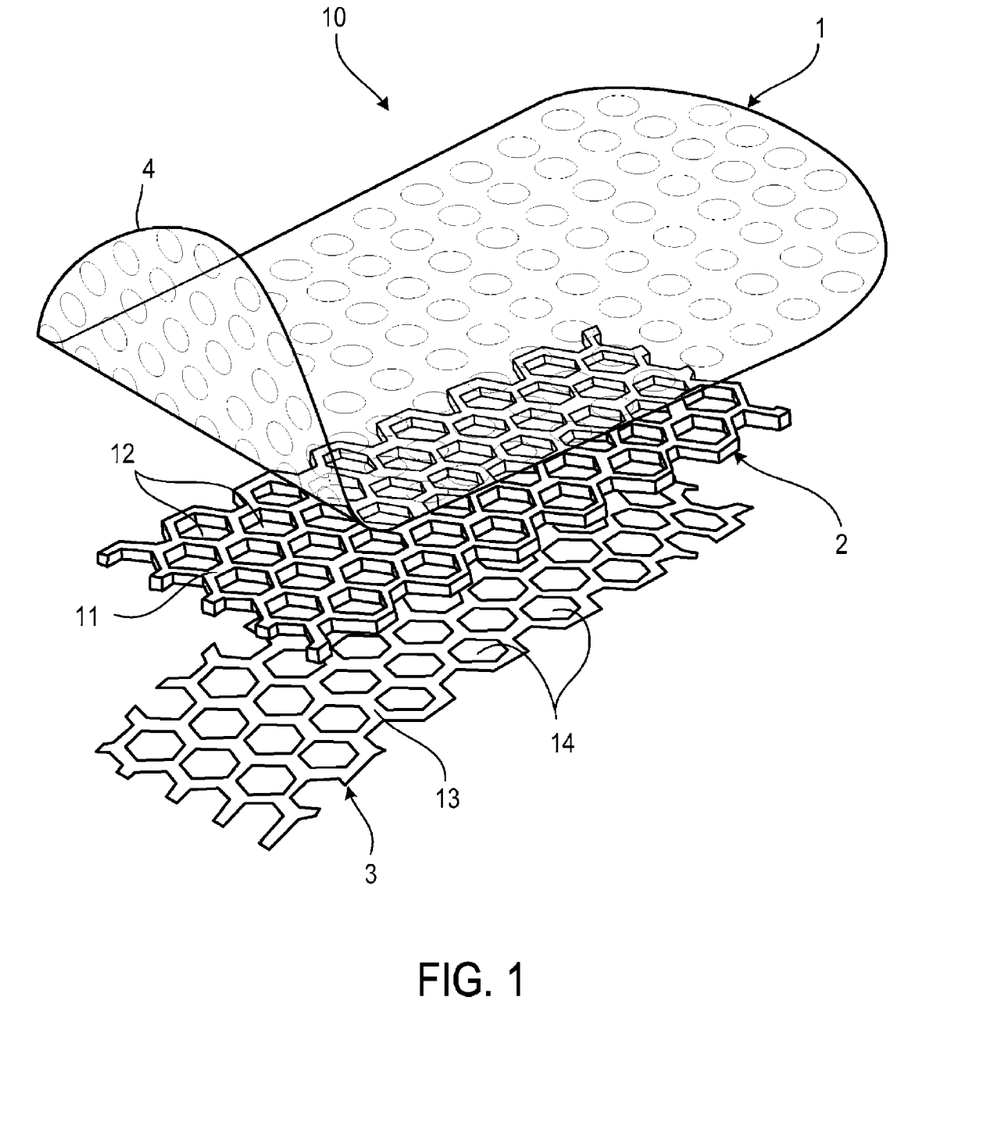
FIG. 1 is an exploded view of a wound dressing.

A wound dressing 10 as illustrated in FIG. 1, includes a transparent upper layer 1, a wound contact layer 3, and an absorbent layer 2 sandwiched between the transparent upper layer 1 and the wound contact layer 3.

Figure 5:
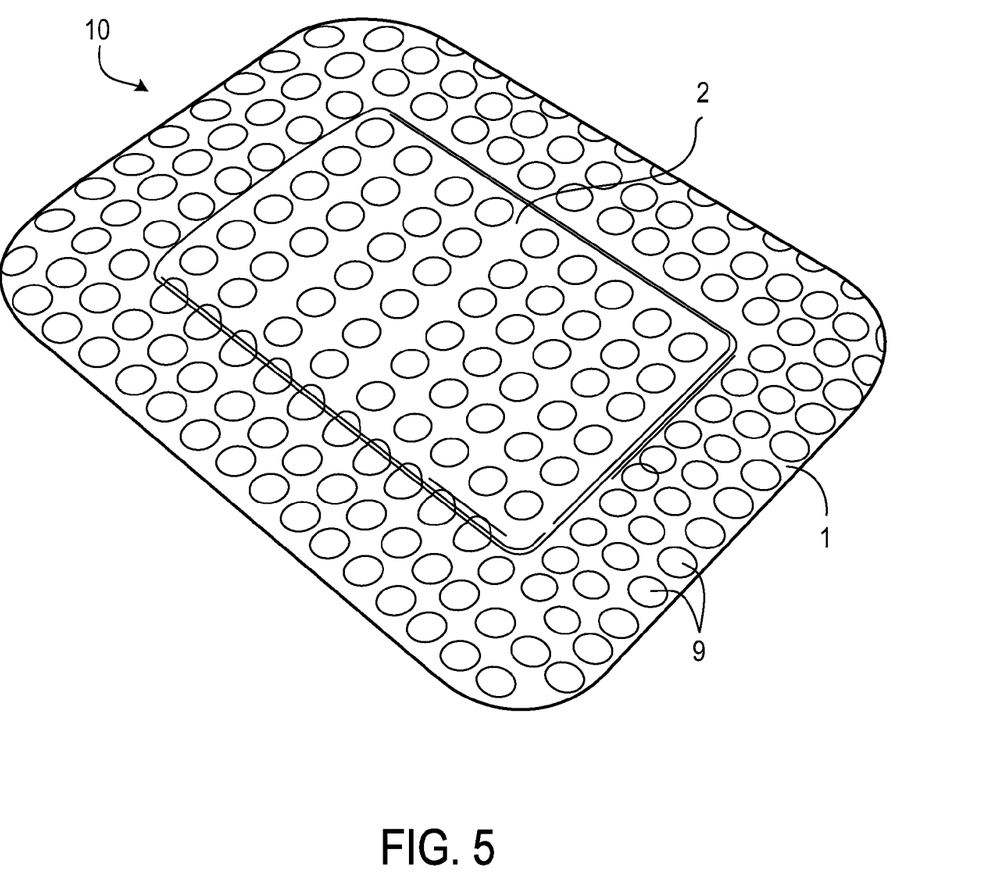
FIG. 5 is a top view of the wound dressing of FIG. 1 illustrating an adhesive pattern on the underside of a transparent upper layer covering an absorbent layer.

The transparent upper layer 1 is made, for example, of a transparent polyurethane film coated on the underside with adhesive 4, for example, a low allergy adhesive such as acrylic. The adhesive is preferably spread in a pattern, for example, a grid of spaced dots 9 (FIG. 5), to increase breathability of the film and comfort of removal. The absorbent layer 2 is made, for example, of a hydrocellular foam, such as polyurethane foam, cut into a lattice pattern. The wound contact layer 3 is made, for example, of a perforated polyurethane film, which is cut into a lattice. The design of the lattice of the wound contact layer 3 substantially mirrors that of the absorbent layer 2, such that when the wound contact layer and the absorbent layer are in contact, the apertures are substantially congruent.

Figure 2A:
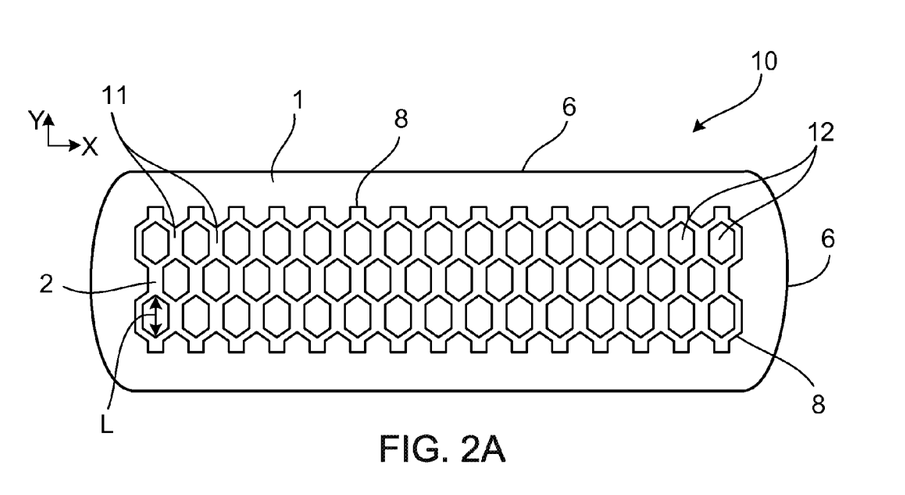
FIG. 2A is a top view of the wound dressing of FIG. 1.

For example, the material used to form the transparent upper layer 1 has a high Moisture Vapor Transmission Rate (MVTR), is waterproof, and acts as a barrier against bacteria, water and dirt. Referring also to FIG. 2A, the peripheral edges 6 of the transparent upper layer extend beyond the peripheral edges 8 of the absorbent layer 2. The adhesive 4 on the underside of the transparent upper layer 1 secures the layer 1 to the absorbent layer 2 and also to the peri-wound area.

The highly absorbent layer 2 includes struts 11 defining a plurality of apertures 12 arranged in a lattice pattern. This arrangement allows for the lateral spread of wound exudate across the lattice to maximize absorbency without impairing visibility, reducing the risk of skin maceration and minimizing the number of dressing changes for cost effective care. The apertures 12, as illustrated, are irregular hexagons, though other shaped apertures can be employed, as discussed below.

The low-adherent wound contact layer 3 includes struts 13 defining a plurality of apertures 14 arranged in a lattice pattern which substantially mirrors that of the pattern for the absorbent layer 2, such that when the wound-contact layer 3 and the absorbent layer 2 are in contact, the apertures are substantially congruent. This facilitates the transfer of the wound exudate into the absorbent layer 2 and ensures visibility through the absorbent layer 2 and the wound contact layer 3 to the wound.

During manufacture, the apertures 12, 14 provided in the absorbent layer 2 and the wound contact layer 3, respectively, can be hole-punched. The two layers can be assembled and then hole-punched or alternatively hole-punched prior to assembly.

The transparent upper layer 1 is, for example, 32 micron thick; the absorbent layer 2 is, for example, 4 mm thick; and the wound contact layer 3 is, for example 28-43 micron (36 micron nominal) thick.

The aperture size is selected to be small enough to allow the exudate to easily reach an absorbent strut 11 but large enough to allow reasonable visibility. For example, the absorbent layer has an absorbent area of not more than 50% of the total area covered, preferably not more than 40%, more preferably not more than 30%, with a repeat pattern of no less than 5 mm in x or y direction, preferably no less than 10 mm in x or y direction, and no greater than 30 mm in x or y direction, preferably no greater than 50 mm in x or y direction (for example, the pattern repeats every 5-50 mm).

The dressing 10 can be provided in a range of sizes and shapes, for example, round, square, oval, etc., allowing clinicians to apply a suitable dressing to a variety of wounds shapes and sizes.

The dressing can be supplied individually wrapped and sterile.

Figure 2B:
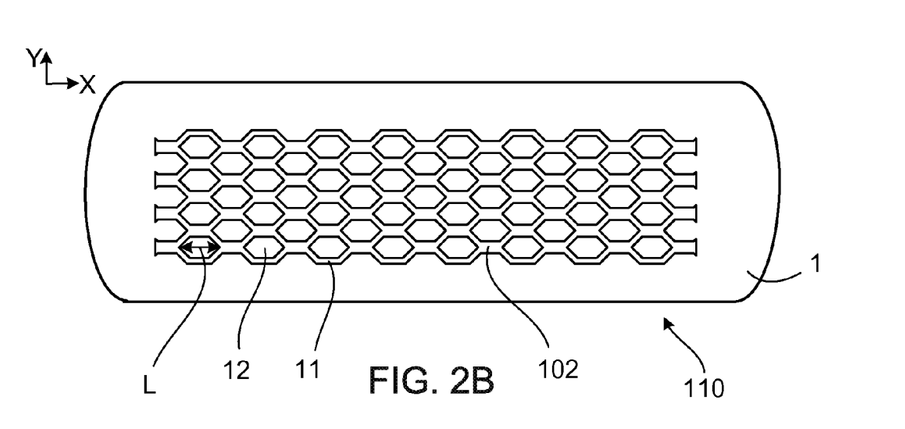
FIG. 2B is a top view of a wound dressing with an alternative configuration of a lattice dressing.
Figure 3A:
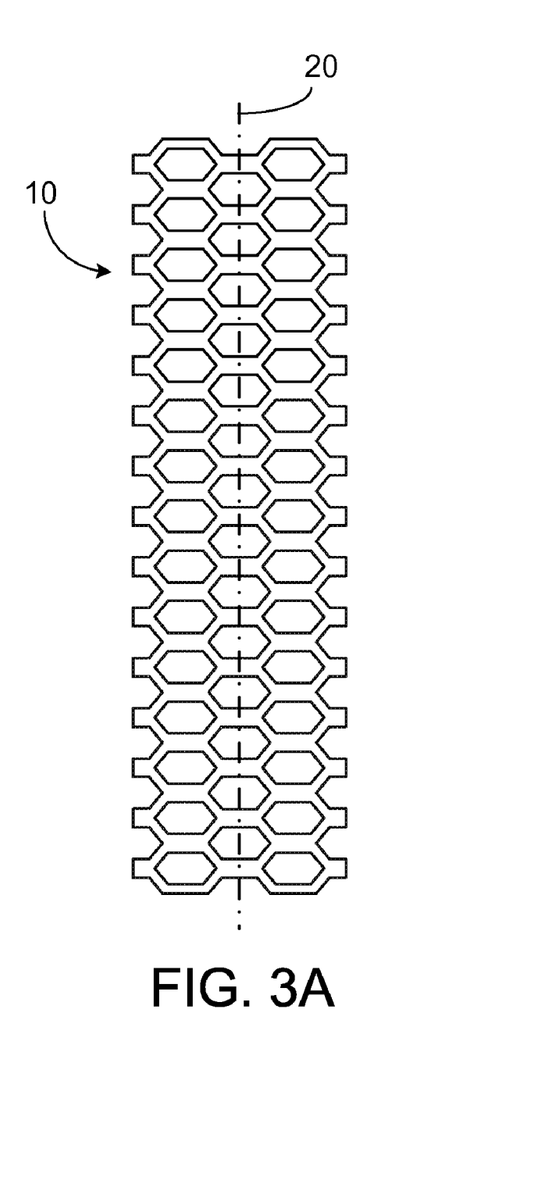
FIG. 3A illustrates the wound dressing of FIG. 2A and the visibility of a suture line covered thereby.
Figure 3B:
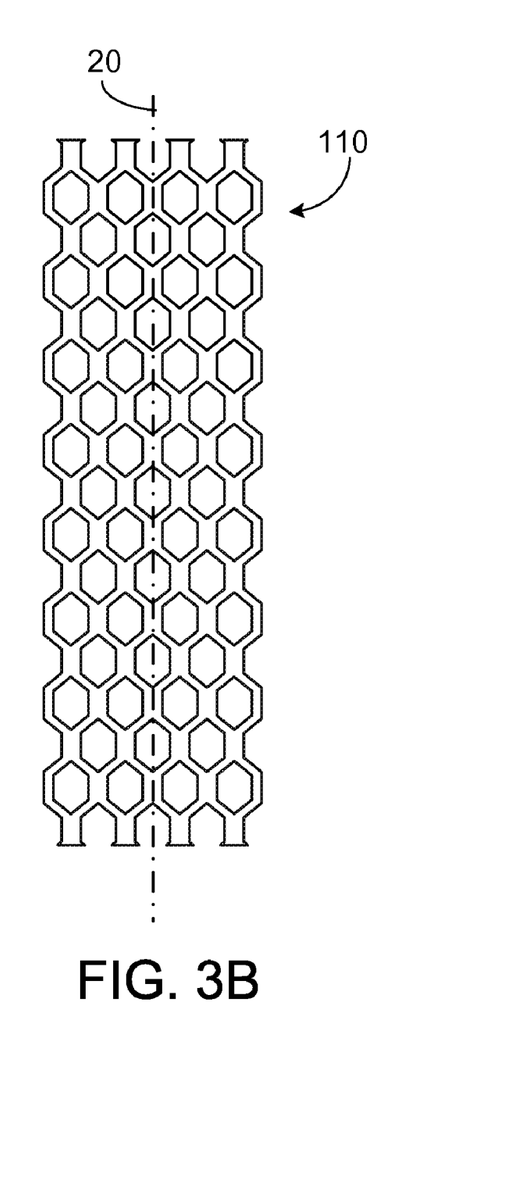
FIG. 3B illustrates the wound dressing of FIG. 2B and the visibility of a suture line covered thereby.

The orientation of the lattice can be changed such that, for example, the long dimension, L, of the aperture 12 in the absorbent layer 102 of the wound dressing 110 is oriented along the x direction (FIG. 2B) rather than the y direction (FIG. 2C). The orientation of the aperture impacts the visibility of a suture line covered by the wound dressing. As illustrated in FIGS. 3A and 3B, wound dressing 10 provides greater visibility of the suture line 20 as compared to wound dressing 110.

Figure 4A:
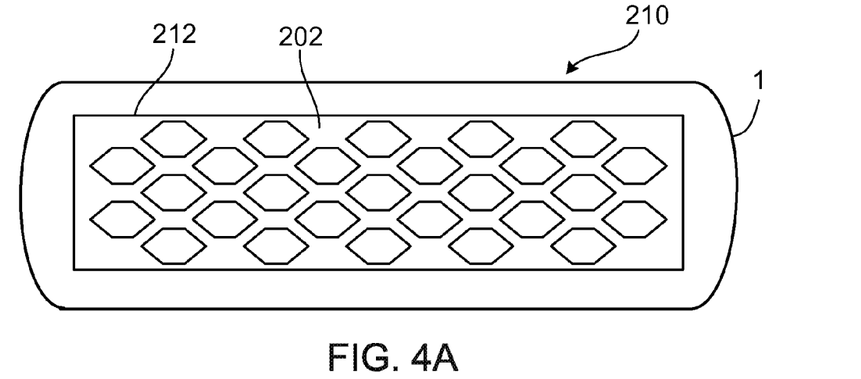
FIGS. 4A-4I are top views of alternative configurations of a wound dressing.
Figure 4B:
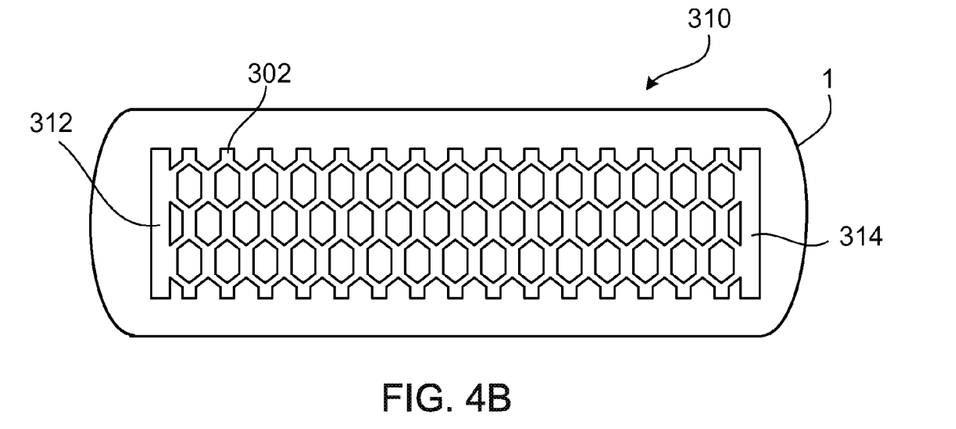
Figure 4C:
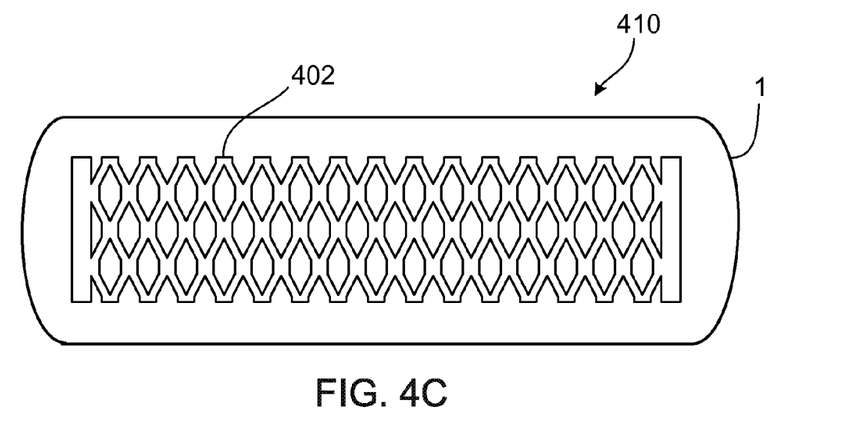
Figure 4D:
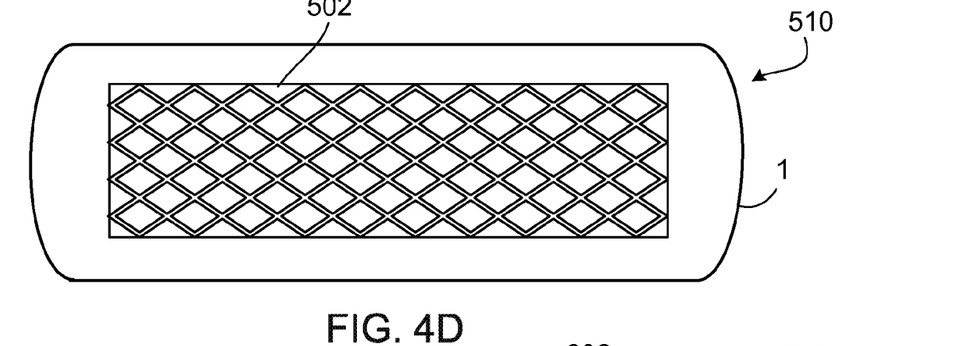
Figure 4E:
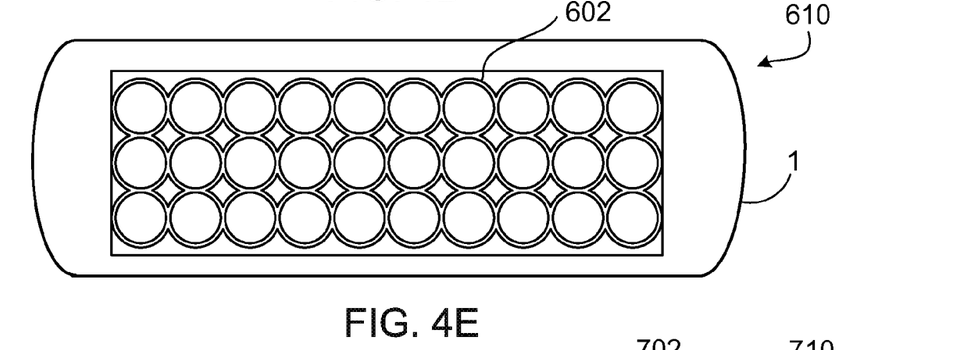
Figure 4F:
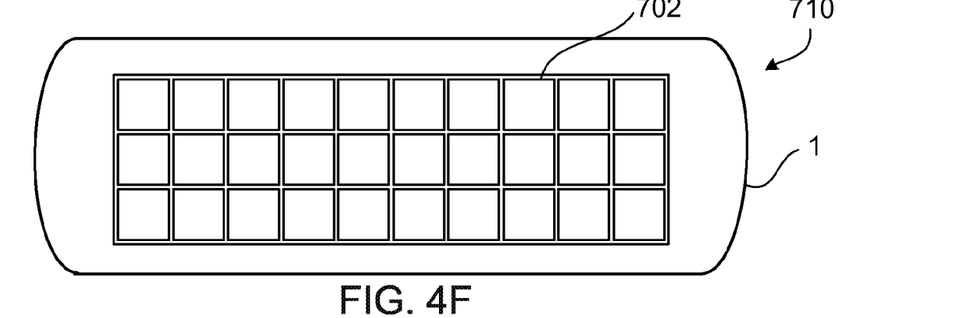
Figure 4G:
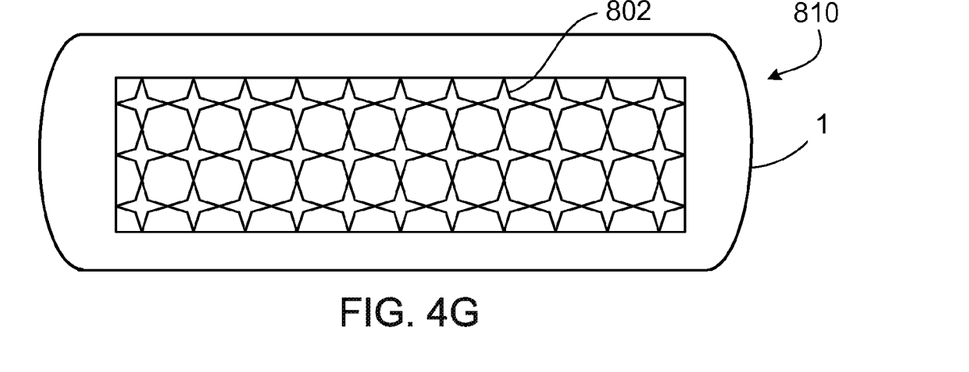
Figure 4H:
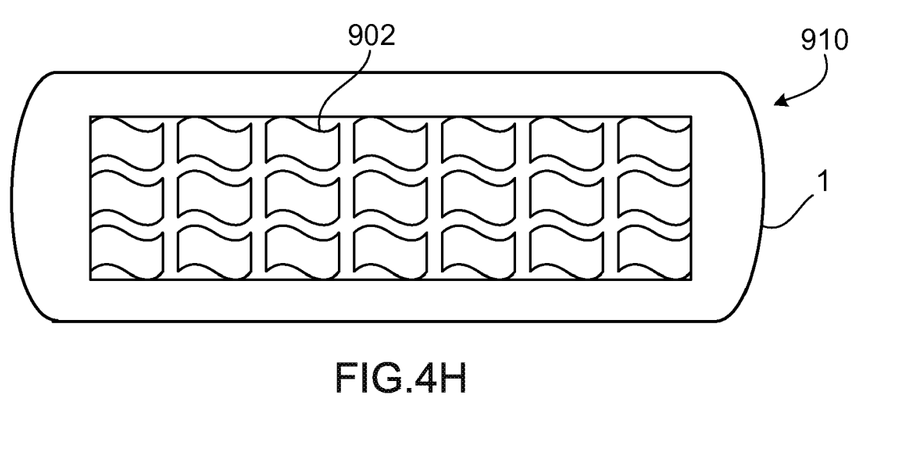
Figure 4I:
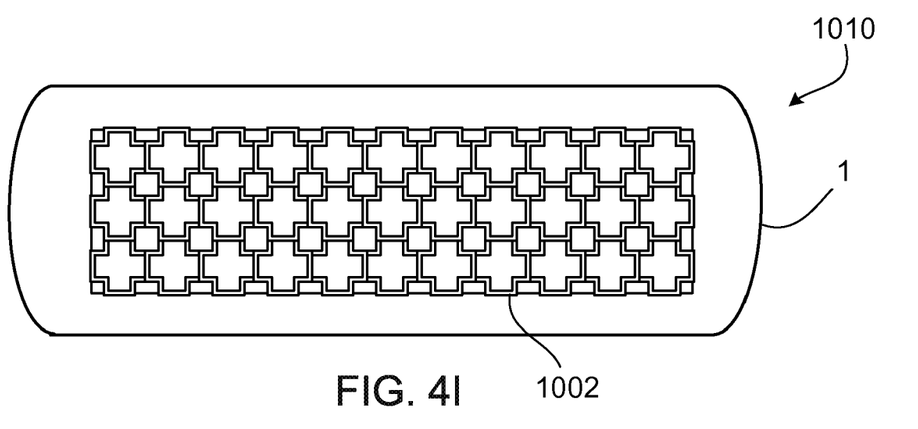

A number of embodiments of the invention have been described. Nevertheless, it will be understood that various modifications may be made without departing from the spirit and scope of the invention. For example, referring to FIGS. 4A-4I, the apertures 12 in the absorbent layer can be provided in various sizes and/or shapes and/or patterns. In FIG. 4A, the absorbent layer 202 of dressing 210 has a straight peripheral border 212. In FIG. 4B, the absorbent layer 302 of dressing 310 terminates in borders 312, 314. Absorbent layer 402 of dressing 410 (FIG. 4C) has apertures that are closer to being diamond shaped, and absorbent layer 502 of dressing 510 (FIG. 4D) has diamond shaped apertures. The apertures in absorbent layers 602, 702 of dressings 610, 710 (FIGS. 4E and 4F) are circular and square shaped, respectively. The apertures of absorbent layer 802 of dressing 810 (FIG. 4G) are regular octagons. The apertures of absorbent layer 902 of dressing 910 (FIG. 4H) are flag-shaped. The apertures of absorbent layer 1002 of dressing 1010 (FIG. 4I) are alternating squares and crosses. The aperture size and shape is selected to provide a balance of visibility and absorbency, and to avoid pooling of fluids on the skin, which can result if fluids have to travel too far to reach the absorbent layer. In addition, the aperture size and shape is selected such that the absorbent layer retains its structure (not break-up) while allowing the dressing to be conformable While not illustrated in the top views of FIGS. 4A-4I, each of the wound dressings further includes a wound contact layer 3.

Accordingly, other embodiments are within the scope of the following claims.

What is claimed is:

1. A wound dressing comprising:
    a substantially transparent layer;
    a low-adherent wound contact layer; and
    an absorbent layer between the transparent layer and the wound contact layer, the absorbent layer defining a plurality of apertures arranged in a lattice pattern, the wound contact layer defining a plurality of apertures arranged in a lattice pattern such that the apertures of the wound contact layer are congruent with the apertures of the absorbent layer.

2. The wound dressing of claim 1 wherein the substantially transparent layer comprises a film.

3. The wound dressing of claim 1 wherein the film comprises an adhesive coating.

4. The wound dressing of claim 1 wherein the absorbent layer comprises foam.

5. The wound dressing of claim 1 wherein the absorbent layer comprises struts defining a plurality of apertures arranged in the lattice pattern.

6. The wound dressing of claim 5 wherein the apertures are irregular hexagons.

7. The wound dressing of claim 1 wherein the absorbent layer has an absorbent area of not more than 50% of the total area covered.

8. The wound dressing of claim 1 wherein the absorbent layer lattice pattern repeats every 5 to 50 mm.

9. The wound dressing of claim 1 wherein the wound contact layer comprises a film.

10. The wound dressing of claim 1 wherein the wound contact layer comprises struts defining a plurality of apertures arranged in the lattice pattern.

11. The wound dressing of claim 1 wherein peripheral edges of the transparent layer extend beyond peripheral edges of the absorbent layer.

12. A method comprising:
    hole punching an absorbent layer and a wound contact layer of a wound dressing such that the absorbent layer defines a plurality of apertures arranged in a lattice pattern and the wound contact layer defines a plurality of apertures arranged in a lattice pattern, and
    arranging the absorbent layer between a transparent layer and the wound contact layer, the apertures of the wound contact layer being congruent with the apertures of the absorbent layer.

* * * * *